United States Patent [19]

Alexander

[11] Patent Number: 5,122,148
[45] Date of Patent: Jun. 16, 1992

[54] DEVICE FOR ASSISTING CHILDBIRTH

[76] Inventor: Gary E. Alexander, 10212 N. Magna Carta, Baton Rouge, La. 70815

[21] Appl. No.: 522,592

[22] Filed: May 14, 1990

[51] Int. Cl.⁵ .............................................. A61B 17/00
[52] U.S. Cl. .................................. 606/122; 606/119; 606/121
[58] Field of Search ............... 606/119, 120, 121, 122, 606/123, 124, 125, 126, 200

[56] References Cited

U.S. PATENT DOCUMENTS

| | | | |
|---|---|---|---|
| 713,166 | 11/1902 | St. Cyr | 606/122 |
| 1,690,942 | 11/1928 | Odell | 606/122 |
| 1,782,814 | 11/1930 | Froehlich | 606/122 |
| 3,139,886 | 7/1964 | Tallman et al. | 604/12 |
| 4,597,391 | 7/1986 | Janko | 606/122 |
| 4,875,482 | 10/1989 | Hariri et al. | 606/122 |

FOREIGN PATENT DOCUMENTS 2925386  1/1981  Fed. Rep. of Germany ...... 606/122

Primary Examiner—Stephen C. Pellegrino
Assistant Examiner—Glenn K. Dawson
Attorney, Agent, or Firm—William David Kiesel; Robert C. Tucker

[57] ABSTRACT

A device to assist in removing a fetus from a woman's vagina during childbirth is provided comprising a pliable, elongated, hollow member sized to fit over the head of the fetus and a size adjustable collar attached at one end of the member to restrict the opening of the hollow member at that end to the desired size.

3 Claims, 2 Drawing Sheets

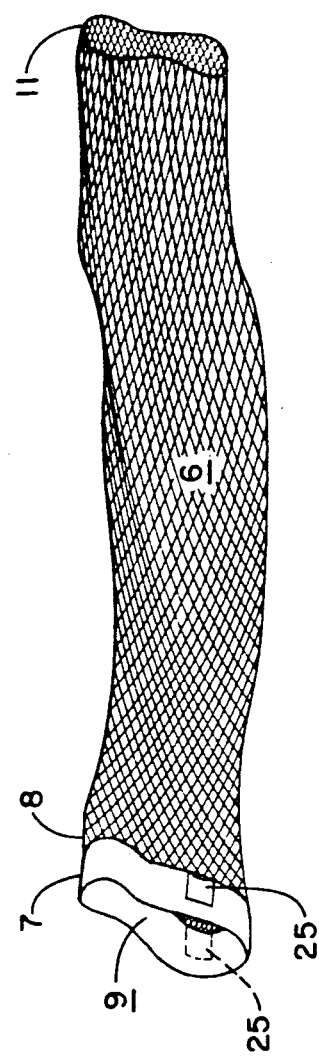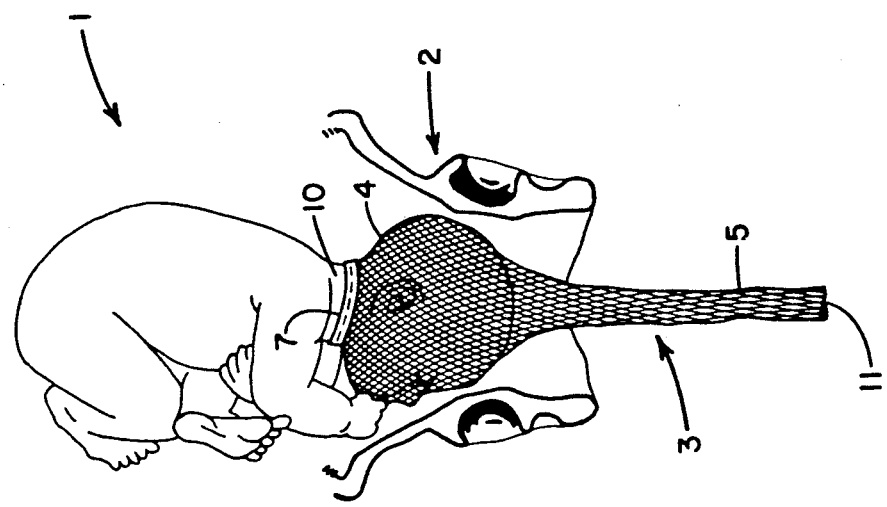
FIGURE 2
FIGURE 1

DEVICE FOR ASSISTING CHILDBIRTH

BACKGROUND OF THE INVENTION

1. Field of the Invention

This invention relates in general to obstetric devices, and more particular to devices useful in removing the baby during vaginal delivery.

2. Prior Art

Today's state of the art obstetrics utilizes various procedures to assist in instances of difficult vaginal deliveries. These procedures basically fall into three categories: version, Caesarian and forceps assisted delivery. In the case of severe cephalo-pelvic disproportion, placenta previa, vaso previa, and other contraindications to vaginal delivery, the "C-Section", whether classic or low transverse, remains the mainstay procedure. However, it has long been recognized that to the extent that C-Section deliveries can be successfully avoided, statistical maternal and fetal benefits will be realized. Even the non-difficult vaginal delivery can benefit from non-traumatic assists.

Many problems may develop during delivery which require assist from the attending obstetrician to successfully remove the baby from the birth canal. One such problem results from the presenting part of the baby, usually its head, descending too slowly. This is particularly true in the case of the primigravida mother. Even with a completely dilated and effaced cervix, and an adequate pelvis, a fetus might refuse to descend beyond station "+1", especially when the mother is suffering from contraction exhaustion. This can remain a problem even with an assist from administration of oxytocin (Pitocin). This problem is frequently exacerbated by anesthesia, particularly in the instance of epidural anesthesia which frequently produces induced non-beneficial partial atony of the engaged and dedicated muscles. Such partial atony frequently results in non-beneficial, and sometimes hazardous, prolongation of labor. Station "+1" is considered midpelvis and in the usual case is considered too high for a forceps assisted delivery. The risks to the fetus with forceps application at this level are extreme. Forceps cannot be safely used until the presenting part is at least at station "+2", and preferably between stations "+2" and "+3", which is the floor of the perineum.

Modern obstetrics has not developed an alternative to the use of forceps when an assisted natural delivery is indicated, such as when the fetus is consistently exhibiting late decelerations of heartbeat following contractions or is exhibiting nonvariability of the baseline heartbeat rate. Obstetrical forceps are typically, in their various types two bladed affairs which are blindly inserted one blade at a time in a hopefully temporal-cheek position and then articulated together before assisting traction is applied. Actual traction is exerted slightly below or underneath the mandibles. The traction is point concentrated and slippage of the forceps is increased because of natural lubrication, refusal of the fetal skull to conform to existing forceps design, and other known myriad of variables that vary from one fetus-to-pelvis physical relationship to another.

Even proper positioning of the forceps can result in harm to the fetus. For example, in instances of minimal cephalo-pelvic disproportion, the insertion of one blade of the forceps can exacerbate any slight deficiency in birth canal adequacy. In addition the softness, or pliability, of the fetal skull, coupled with the existence of sutures which separate the plates of the skull, render the skull susceptible to trauma associated with metal forceps assisted deliveries.

The problems associated with forceps assisted deliveries is well known, and many attempts have been made to improve forceps design. Examples of the current state of the art in forceps design can be seen in the following patents: Leonard E. Laufe U.S. Pat. No. 3,550,595 entitled "Obstetrical Forceps" and issued on Dec. 29, 1970; Hector Salinas Benavides U.S. Pat. No. 3,605,748 entitled "Obstetrical Forceps" and issued on Sep. 20, 1971; Hamo M. Derslookian U.S. Pat. No. 3,665,925 entitled "Obstetrical Forceps" and issued on May 30, 1972; Brenton R. Lower et al U.S. Pat. No. 3,785,381 entitled "Pressure Sensing Obstetrical Forceps" and issued on Jan. 15, 1974; Leonard E Laufe et al U.S. Pat. No. 3,789,849 entitled "Obstetrical Forceps" and issued on Feb. 5, 1974; and William O. Vennard U.S. Pat. No. 3,794,044 entitled "Delivery Forceps" and issued on Feb. 26, 1974.

Despite the long felt need and the large amount of time and effort spent to develop an alternative to forceps, the only assisting device developed which has seen some application is a vacuum extractor. Because of the difficulty in the safe use of this device, it has not proven to be successful and its use has in large measure been abandoned.

OBJECTS AND SUMMARY OF THE INVENTION

It is therefore an object of this invention to provide an assisting device for childbirth which can safely perform substantially all of the functions of forceps.

Another object of this invention is to provide an assisting device for childbirth that is easy to use and reduces the risk of injury to the fetus during childbirth.

Still another object of this invention is to provide an assisting device for childbirth that can be quickly applied to the skull of the fetus by the attending obstetrician.

Still other objects and advantages of this invention shall become apparent from the ensuing descriptions of the invention.

Accordingly,

BRIEF DESCRIPTION OF THE DRAWINGS

FIG. 1 is cutaway view of an unborn infant positioned for vaginal delivery to which has been attached a preferred embodiment of this invention.

FIG. 2 is a three dimensional view of one preferred embodiment of the this invention.

PREFERRED EMBODIMENTS OF THE INVENTION

Figure 3:
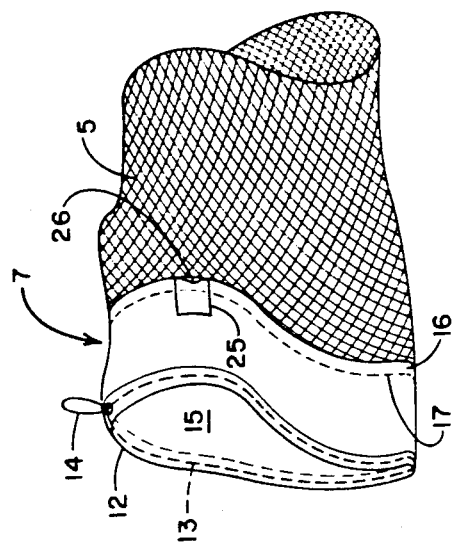
FIG. 3 is an enlarged view of one preferred embodiment of the closure means forming part of this invention.

Referring now to FIG. 1 a fetus, generally denoted by numeral 1, is depicted positioned in a cutaway of a portion of a woman's birth canal 2 having the childbirth assist device 3 attached to its head 4 and trailing outside of the vagina area of the birth canal 2.

In its broadest context as shown in FIG. 2 the device 3 comprises an elongated sock-like member 5 open at both ends not only to allow a physician to fit his hand and arm in passageway 6 of member 5 for rotational purposes, but also to allow the head 4 to fit into passageway 6. In addition device 3 comprises a collar 7 attached at one end 8 of member 5 which can be adjusted to restrict the size of opening 9 formed at end 8.

In one preferred embodiment member 5 is constructed from material having some elasticity characteristics, and more preferably from a material selected from a group consisting of natural fibers or man-made plastic fibers. Natural fibers could include cotton, linen and silk. Plastic fibers could include nylon, dacron and rayon. Preferably the degree of elasticity should be at least to a degree such that the material would begin stretch before the pulling force exceeded a predetermined amount. That amount would depend on the stage of development of the fetus, as well as other known factors. The degree of elasticity is preferably set so the pulling force is less than that which would harm the fetus. Member 5 is also preferably pliable so that it can be shaped and easily moved in position about head 4. In another preferred embodiment the material will be constructed from a mesh material, the size of the mesh would preferably be sufficiently small enough to reduce chances of non-beneficial oral ingestion of toxic meconium by the fetus. In still another preferred embodiment the fabrics would be sterilized and lubricated with K-Y jelly to reduce or prevent the fabric from absorbing the natural lubricants within the womb. K-Y jelly is a brand name for an antiseptic non-fatty and soluble lubricating jelly product sold by Johnson & Johnson.

In one embodiment as shown in FIG. 2, collar 7 is constructed of an elastic material which can be stretched to fit about head 4 and then will contract to an extent to fit loosely about the neck area 10 of the fetus 1. In this manner collar 7 will not choke the fetus 1, but also will not easily slip over the head 4 when the physician pulls on end 11 of member 5 during the delivery process as described below.

In another embodiment as shown in FIG. 3, collar 7 is constructed from an pliable material wherein one edge section 12 has been folded over and stitched to itself to form a drawstring pocket 13 in which drawstring 14 has been placed. When drawstring 14 is pulled opening 15 is restricted. The other edge section 16 of collar 7 is stitched or otherwise connected to member 5 along line 17.

Figure 4:
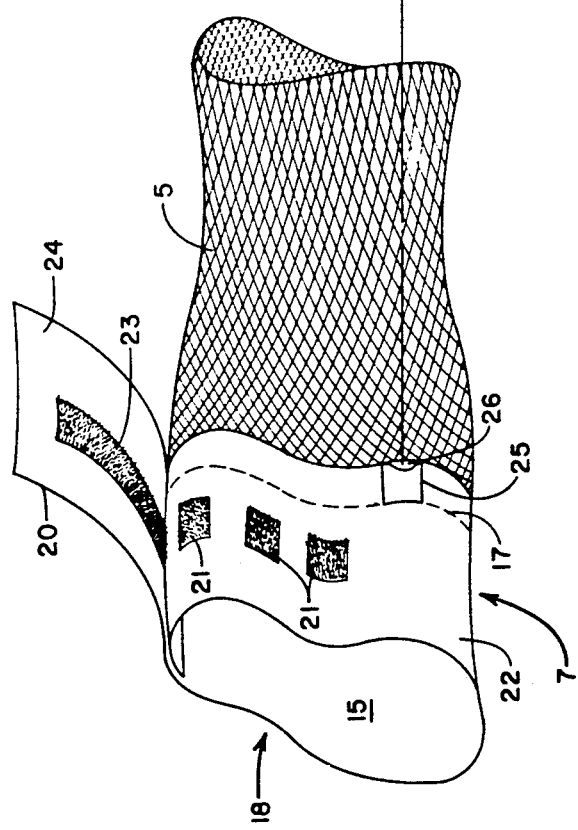
FIG. 4 is an enlarged view of another preferred embodiment of the closure means forming part of this invention.

In a third embodiment as shown in FIG. 4, collar 7 is constructed of a strip 18 of pliable material having one section 19 stitched or otherwise connected substantially about the perimeter of end 8, and having another section 20 that can extend over a portion of the first section 19. Strips 21 of Velcro or similar material are attached to side 22 of section 19 in a position to be alignable with at least a portion of the strips 23 of Velcro or similar material attached to side 24 of section 20. The size of opening 15 can be adjusted by changing the alignment of the strips 21 and 23. Opening size is then maintained by contacting the overlapping sections of the strips to one another. Velcro is a registered trademark of VELCRO INDUSTRIES, B. V. (NETHERLANDS CORPORATION) identifying hook and loop fastener systems.

In a preferred embodiment as illustrated in FIG. 2-4, collar 7 is provided with one or more pockets, preferably two or more, formed by a piece 25 of fabric that is attached on three sides to collar 7 to form an opening 26 facing toward member 5. The opening 26 will be large enough so that one end of wand 27 can be inserted through the opening. Wand 27 is preferably constructed from a flexible material, such as plastic, that would will allow it to conform to the shape of the fetus' head, yet rigid enough to allow it to be used to push collar 7 around the fetus' head when positioning device 3.

In operation the device 3 is first positioned on the top of the fetus' head 4 with the wands 27 fitted into pockets 25. The wands 27 are then maneuvered by pushing the ends of each wand 27 against the inside walls of their respective pocket 25 until the device is slipped over the fetus' head. When the collar 7 extends posterior to the head 4 the physician then adjusts collar 7 so that it fits loosely about neck area lo, but is restricted so as not to easily slip over the head 4. The physician then grabs the end 11 and applies a pulling force which will cause the collar 7 to exert an equalized and evenly distributed pulling force under the smallest circumference of the head 4. This pulling force will assist the mother in the natural childbirth or in positioning the fetus 1 closer to position "+2" and "+3" where if needed forceps can be used more safely. In many cases device 3 may eliminate the need to use forceps during the delivery.

There are of course other alternate embodiments which are obvious from the foregoing descriptions of the invention which are intended to be included within the scope of the invention as defined by the following claims.

What I claim is:

1. A device for assisting in the removal of a fetus from a woman's birth canal during childbirth comprising:
    (a) an elongated member having a tubular passageway therein, said elongated member being open at both ends, having at least one of the end openings sized to allow the head of said fetus to pass into said tubular passageway of said member, said tubular passageway being sized to receive said head,
    (b) a pliable collar attached to and extending about said one end of said member, said collar having at least one pocket which opens in a direction opposite from said one end and being adjustable to restrict the opening of said one end to permit said head to enter said tubular passageway and then adjustable to prevent said head from being pulled from said passageway when a pulling force is applied to said member opposite said opening, wherein said collar comprises:
        (i) a strip of material a first section of which is attached substantially about said one end,
        (ii) a second section which is sized to be positioned over at least a portion of said first section, and
        (iii) hook and loop type fastener strips being attached to said portion of said first section and to an adjacent side of said second section to seal said second section to said first section in a desired position and
    (c) at least one flexible, elongated wand having one end sized to be insertable in said pocket and sized to cause said collar to be positioned about said head when sufficient force is applied by said wand to said collar.

2. A device according to claim 1 wherein said member is constructed from a mesh material.

3. A device according to claim 2 wherein said material is selected from a group consisting of natural fibers or plastic fibers or a combination of natural fibers or plastic fibers.

* * * * *